US008541450B2

(12) United States Patent
Pfrengle et al.

(10) Patent No.: US 8,541,450 B2
(45) Date of Patent: Sep. 24, 2013

(54) PROCESS FOR THE PREPARATION OF CHIRAL 8-(3-AMINOPIPERIDIN-1YL)-XANTHINES

(75) Inventors: Waldemar Pfrengle, Biberach (DE); Thorsten Pachur, Schwendi (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 712 days.

(21) Appl. No.: 12/413,851

(22) Filed: Mar. 30, 2009

(65) Prior Publication Data

US 2009/0192314 A1 Jul. 30, 2009

Related U.S. Application Data

(62) Division of application No. 11/267,235, filed on Nov. 4, 2005, now Pat. No. 7,820,815.

(30) Foreign Application Priority Data

Nov. 5, 2004 (DE) .......................... 10 2004 05 4054

(51) Int. Cl.
*A61K 31/405* (2006.01)
*A61K 31/445* (2006.01)
*C07D 209/04* (2006.01)
*C07D 211/22* (2006.01)
*C07D 401/00* (2006.01)
*C07D 421/00* (2006.01)

(52) U.S. Cl.
USPC ........... 514/315; 514/319; 514/323; 514/415; 546/221; 546/268.1; 546/276.4; 546/277.1; 548/469; 548/470

(58) Field of Classification Search
USPC ......................................... 514/323; 546/221
See application file for complete search history.

(56) References Cited

U.S. PATENT DOCUMENTS

| | | | |
|---|---|---|---|
| 2,056,046 A | 9/1936 | Fourneau | |
| 2,375,138 A | 5/1945 | Salvin | |
| 2,629,736 A | 2/1953 | Krimmel | |
| 2,730,544 A | 1/1956 | Sahyun | |
| 2,750,387 A | 6/1956 | Krimmel | |
| 2,928,833 A | 3/1960 | Leake et al. | |
| 3,174,901 A | 3/1965 | Sterne | |
| 3,236,891 A | 2/1966 | Seemuller | |
| 3,454,635 A | 7/1969 | Muth | |
| 3,673,241 A | 6/1972 | Marxer | |
| 3,925,357 A | 12/1975 | Okada et al. | |
| 4,005,208 A * | 1/1977 | Bender et al. | 514/320 |
| 4,061,753 A | 12/1977 | Bodor et al. | |
| 4,599,338 A | 7/1986 | Regnier et al. | |
| 4,639,436 A | 1/1987 | Junge et al. | |
| 4,687,777 A | 8/1987 | Meguro et al. | |
| 4,816,455 A | 3/1989 | Schickaneder et al. | |
| 4,873,330 A | 10/1989 | Lindholm | |
| 4,968,672 A | 11/1990 | Jacobson et al. | |
| 5,041,448 A | 8/1991 | Janssens | |
| 5,051,517 A | 9/1991 | Findeisen | |
| 5,084,460 A | 1/1992 | Munson, Jr. et al. | |
| 5,219,870 A | 6/1993 | Kim | |
| 5,223,499 A | 6/1993 | Greenlee | |
| 5,234,897 A | 8/1993 | Findeisen et al. | |
| 5,258,380 A | 11/1993 | Janssens | |
| 5,266,555 A | 11/1993 | Findeisen et al. | |
| 5,273,995 A | 12/1993 | Roth | |
| 5,300,298 A | 4/1994 | LaNoue | |
| 5,329,025 A | 7/1994 | Wong et al. | |
| 5,332,744 A | 7/1994 | Chakravarty et al. | |
| 5,389,642 A | 2/1995 | Dorsch | |
| 5,399,578 A | 3/1995 | Buhlmayer et al. | |
| 5,407,929 A | 4/1995 | Takahashi et al. | |
| 5,470,579 A | 11/1995 | Bonte et al. | |
| 5,591,762 A | 1/1997 | Hauel et al. | |
| 5,594,003 A | 1/1997 | Hauel et al. | |
| 5,602,127 A | 2/1997 | Hauel et al. | |
| 5,614,519 A | 3/1997 | Hauel et al. | |
| 5,719,279 A | 2/1998 | Kufner-Muhl et al. | |
| 5,728,849 A | 3/1998 | Bouchard et al. | |
| 5,753,635 A | 5/1998 | Buckman | |
| 5,830,908 A | 11/1998 | Grunenberg et al. | |
| 5,958,951 A | 9/1999 | Ahrndt et al. | |
| 5,965,555 A | 10/1999 | Gebert et al. | |
| 5,965,592 A | 10/1999 | Buhlmayer et al. | |
| 6,107,302 A | 8/2000 | Carter et al. | |
| 6,248,758 B1 | 6/2001 | Klokkers et al. | |
| 6,303,661 B1 | 10/2001 | Demuth | |
| 6,342,601 B1 | 1/2002 | Bantick | |
| 6,372,940 B1 | 4/2002 | Cavazza | |
| 6,548,481 B1 | 4/2003 | Demuth et al. | |
| 6,579,868 B1 | 6/2003 | Asano | |
| 6,727,261 B2 | 4/2004 | Gobbi et al. | |
| 6,784,195 B2 | 8/2004 | Hale et al. | |
| 6,821,978 B2 | 11/2004 | Chackalamannil | |
| 6,869,947 B2 | 3/2005 | Kanstrup | |
| 7,060,722 B2 | 6/2006 | Kitajima | |
| 7,074,794 B2 | 7/2006 | Kitajima | |
| 7,074,798 B2 | 7/2006 | Yoshikawa | |
| 7,074,923 B2 | 7/2006 | Dahanukar | |
| 7,109,192 B2 | 9/2006 | Hauel | |
| 7,179,809 B2 | 2/2007 | Eckhardt | |
| 7,183,280 B2 | 2/2007 | Himmelsbach | |
| 7,192,952 B2 | 3/2007 | Kanstrup | |
| 7,217,711 B2 | 5/2007 | Eckhardt | |
| 7,235,538 B2 | 6/2007 | Kanstrup et al. | |
| 7,291,642 B2 | 11/2007 | Kauffmann-Hefner et al. | |

(Continued)

FOREIGN PATENT DOCUMENTS

CA 1123437 A1 5/1982
CA 2136288 A1 5/1995

(Continued)

OTHER PUBLICATIONS

Augusti, et al., Chem. Comm., 2002, 2242-2243.*

(Continued)

*Primary Examiner* — Susannah Chung
(74) *Attorney, Agent, or Firm* — Michael P. Morris; David L. Kershner

(57) ABSTRACT

The invention relates to enantiomerically pure 3-(phthalimido)piperidines and processes for preparing enantiomerically pure 3-(phthalimido)piperidines.

2 Claims, No Drawings

(56) References Cited

U.S. PATENT DOCUMENTS

| | | |
|---|---|---|
| 7,361,687 B2 | 4/2008 | Barth et al. |
| 7,393,847 B2 | 7/2008 | Eckhardt et al. |
| 7,407,955 B2 | 8/2008 | Himmelsbach et al. |
| 7,432,262 B2 | 10/2008 | Eckhardt et al. |
| 7,439,370 B2 | 10/2008 | Eckhardt |
| 7,470,716 B2 | 12/2008 | Eckhardt et al. |
| 7,476,671 B2 | 1/2009 | Eckhardt et al. |
| 7,482,337 B2 | 1/2009 | Himmelsbach et al. |
| 7,495,002 B2 | 2/2009 | Langkopf et al. |
| 7,495,003 B2 | 2/2009 | Eckhardt et al. |
| 7,495,005 B2 | 2/2009 | Himmelsbach et al. |
| 7,501,426 B2 | 3/2009 | Himmelsbach et al. |
| 7,550,455 B2 | 6/2009 | Himmelsbach et al. |
| 7,560,450 B2 | 7/2009 | Eckhardt et al. |
| 7,566,707 B2 | 7/2009 | Eckhardt et al. |
| 7,569,574 B2 | 8/2009 | Maier et al. |
| 7,579,449 B2 | 8/2009 | Eckhardt et al. |
| 7,645,763 B2 | 1/2010 | Himmelsbach et al. |
| 7,718,666 B2 | 5/2010 | Boehringer et al. |
| 7,799,782 B2 | 9/2010 | Munson et al. |
| 7,820,815 B2 | 10/2010 | Pfrengle et al. |
| 8,071,583 B2 | 12/2011 | Himmelsbach |
| 8,106,060 B2 | 1/2012 | Pfrengle et al. |
| 8,119,648 B2 | 2/2012 | Himmelsbach et al. |
| 8,178,541 B2 | 5/2012 | Himmelsbach et al. |
| 8,232,281 B2 | 7/2012 | Dugi et al. |
| 2001/0020006 A1 | 9/2001 | Demuth et al. |
| 2001/0051646 A1 | 12/2001 | Demuth et al. |
| 2002/0137903 A1 | 9/2002 | Ellsworth et al. |
| 2002/0161001 A1 | 10/2002 | Kanstrup |
| 2002/0169174 A1 | 11/2002 | Chackalamannil et al. |
| 2002/0198205 A1 | 12/2002 | Himmelsbach |
| 2003/0105077 A1 | 6/2003 | Kanstrup et al. |
| 2003/0114390 A1 | 6/2003 | Washburn et al. |
| 2003/0166578 A1 | 9/2003 | Arch et al. |
| 2003/0199528 A1 | 10/2003 | Kanstrup |
| 2003/0224043 A1 | 12/2003 | Appel et al. |
| 2003/0232987 A1 | 12/2003 | Dahanukar et al. |
| 2003/0236272 A1 | 12/2003 | Carr |
| 2004/0023981 A1 | 2/2004 | Ren et al. |
| 2004/0034014 A1 | 2/2004 | Kanstrup et al. |
| 2004/0063725 A1 | 4/2004 | Barth et al. |
| 2004/0077645 A1 | 4/2004 | Himmelsbach et al. |
| 2004/0082570 A1 | 4/2004 | Yoshikawa |
| 2004/0087587 A1 | 5/2004 | Himmelsbach |
| 2004/0097510 A1 | 5/2004 | Himmelsbach et al. |
| 2004/0116328 A1 | 6/2004 | Yoshikawa et al. |
| 2004/0122228 A1 | 6/2004 | Maier |
| 2004/0126358 A1 | 7/2004 | Warne et al. |
| 2004/0138214 A1 | 7/2004 | Himmelsbach et al. |
| 2004/0138215 A1 | 7/2004 | Eckhardt |
| 2004/0166125 A1 | 8/2004 | Himmelsbach |
| 2004/0180925 A1 | 9/2004 | Matsuno et al. |
| 2005/0020574 A1 | 1/2005 | Hauel et al. |
| 2005/0026921 A1 | 2/2005 | Eckhardt |
| 2005/0032804 A1 | 2/2005 | Cypes et al. |
| 2005/0065145 A1 | 3/2005 | Cao et al. |
| 2005/0070594 A1 | 3/2005 | Kauschke et al. |
| 2005/0130985 A1 | 6/2005 | Himmelsbach |
| 2005/0143377 A1 | 6/2005 | Himmelsbach et al. |
| 2005/0171093 A1 | 8/2005 | Eckhardt et al. |
| 2005/0187227 A1 | 8/2005 | Himmelsbach et al. |
| 2005/0203095 A1 | 9/2005 | Eckhardt |
| 2005/0234108 A1 | 10/2005 | Himmelsbach et al. |
| 2005/0234235 A1 | 10/2005 | Eckhardt et al. |
| 2005/0239778 A1 | 10/2005 | Konetzki et al. |
| 2005/0256310 A1 | 11/2005 | Hulin et al. |
| 2005/0261352 A1 | 11/2005 | Eckhardt |
| 2005/0266080 A1 | 12/2005 | Desai et al. |
| 2005/0276794 A1 | 12/2005 | Papas et al. |
| 2006/0004074 A1 | 1/2006 | Eckhardt |
| 2006/0039974 A1 | 2/2006 | Akiyama et al. |
| 2006/0047125 A1 | 3/2006 | Leonardi et al. |
| 2006/0058323 A1 | 3/2006 | Eckhardt et al. |
| 2006/0063787 A1 | 3/2006 | Yoshikawa |
| 2006/0079541 A1 | 4/2006 | Langkopf |
| 2006/0094722 A1 | 5/2006 | Yasuda |
| 2006/0100199 A1 | 5/2006 | Yoshikawa et al. |
| 2006/0111379 A1 | 5/2006 | Guillemont et al. |
| 2006/0142310 A1 | 6/2006 | Pfrengle et al. |
| 2006/0154866 A1 | 7/2006 | Chu et al. |
| 2006/0173056 A1 | 8/2006 | Kitajima |
| 2006/0205711 A1 | 9/2006 | Himmelsbach |
| 2006/0205943 A1 | 9/2006 | Dahanukar et al. |
| 2006/0247226 A1 | 11/2006 | Himmelsbach |
| 2006/0270668 A1 | 11/2006 | Chew et al. |
| 2007/0027168 A1 | 2/2007 | Pfrengle et al. |
| 2007/0060530 A1 | 3/2007 | Christopher et al. |
| 2007/0088038 A1 | 4/2007 | Eckhardt |
| 2007/0093659 A1 | 4/2007 | Bonfanti |
| 2007/0142383 A1 | 6/2007 | Eckhardt |
| 2007/0185091 A1 | 8/2007 | Himmelsbach et al. |
| 2007/0196472 A1 | 8/2007 | Kiel et al. |
| 2007/0197522 A1 | 8/2007 | Edwards et al. |
| 2007/0219178 A1 | 9/2007 | Muramoto |
| 2007/0259900 A1 | 11/2007 | Sieger et al. |
| 2007/0281940 A1 | 12/2007 | Dugi |
| 2007/0299076 A1 | 12/2007 | Piotrowski et al. |
| 2008/0039427 A1 | 2/2008 | Ray et al. |
| 2008/0107731 A1 | 5/2008 | Kohlrausch et al. |
| 2008/0108816 A1 | 5/2008 | Zutter |
| 2008/0249089 A1 | 10/2008 | Himmelsbach et al. |
| 2008/0255159 A1 | 10/2008 | Himmelsbach et al. |
| 2008/0312243 A1 | 12/2008 | Eckhardt et al. |
| 2008/0318922 A1 | 12/2008 | Nakahira et al. |
| 2009/0023920 A1 | 1/2009 | Eckhardt |
| 2009/0088408 A1 | 4/2009 | Meade et al. |
| 2009/0088569 A1 | 4/2009 | Eckhardt et al. |
| 2009/0093457 A1 | 4/2009 | Himmelsbach et al. |
| 2009/0131432 A1 | 5/2009 | Himmelsbach et al. |
| 2009/0136596 A1 | 5/2009 | Munson et al. |
| 2009/0137801 A1 | 5/2009 | Himmelsbach et al. |
| 2009/0192314 A1 | 7/2009 | Pfrengle et al. |
| 2009/0325926 A1 | 12/2009 | Himmelsbach |
| 2010/0074950 A1 | 3/2010 | Sesha |
| 2010/0173916 A1 | 7/2010 | Himmelsbach et al. |
| 2010/0183531 A1 | 7/2010 | Johncock et al. |
| 2010/0204250 A1 | 8/2010 | Himmelsbach et al. |
| 2011/0046076 A1 | 2/2011 | Eickelmann et al. |
| 2011/0065731 A1 | 3/2011 | Dugi et al. |
| 2011/0092510 A1 | 4/2011 | Klein et al. |
| 2011/0098240 A1 | 4/2011 | Dugi et al. |
| 2011/0112069 A1 | 5/2011 | Himmelsbach et al. |
| 2011/0144083 A1 | 6/2011 | Himmelsbach et al. |
| 2011/0144095 A1 | 6/2011 | Himmelsbach et al. |
| 2011/0190322 A1 | 8/2011 | Klein et al. |
| 2011/0195917 A1 | 8/2011 | Dugi et al. |
| 2011/0206766 A1 | 8/2011 | Friedl et al. |
| 2011/0263493 A1 | 10/2011 | Dugi et al. |
| 2011/0263617 A1 | 10/2011 | Mark et al. |
| 2011/0275561 A1 | 11/2011 | Graefe-Mody et al. |
| 2011/0301182 A1 | 12/2011 | Dugi |
| 2012/0003313 A1 | 1/2012 | Kohlrausch et al. |
| 2012/0035158 A1 | 2/2012 | Himmelsbach et al. |
| 2012/0040982 A1 | 2/2012 | Himmelsbach et al. |
| 2012/0094894 A1 | 4/2012 | Graefe-Mody et al. |
| 2012/0107398 A1 | 5/2012 | Schneider et al. |
| 2012/0121530 A1 | 5/2012 | Klein et al. |
| 2012/0122776 A1 | 5/2012 | Graefe-Mody et al. |
| 2012/0129874 A1 | 5/2012 | Sieger et al. |
| 2012/0142712 A1 | 6/2012 | Pfrengle et al. |
| 2012/0165251 A1 | 6/2012 | Klein et al. |
| 2012/0208831 A1 | 8/2012 | Himmelsbach et al. |
| 2012/0219622 A1 | 8/2012 | Kohlrausch et al. |
| 2012/0219623 A1 | 8/2012 | Meinicke |
| 2012/0252782 A1 | 10/2012 | Himmelsbach et al. |
| 2012/0252783 A1 | 10/2012 | Himmelsbach et al. |

FOREIGN PATENT DOCUMENTS

| | | |
|---|---|---|
| CA | 2418656 A1 | 2/2002 |
| CA | 2496325 A1 | 3/2004 |
| CA | 2496249 A1 | 4/2004 |
| CA | 2505389 A1 | 5/2004 |
| CA | 2508233 A1 | 6/2004 |

| | | | | | | |
|---|---|---|---|---|---|---|
| CA | 2529729 | A1 | 12/2004 | WO | 0177110 A1 | 10/2001 |
| CA | 2543074 | A1 | 6/2005 | WO | 0197808 A1 | 12/2001 |
| CA | 2555050 | A1 | 9/2005 | WO | 02/02560 A2 | 1/2002 |
| CA | 2556064 | A1 | 9/2005 | WO | 02/14271 A1 | 2/2002 |
| CA | 2558067 | A1 | 10/2005 | WO | 02/24698 A1 | 3/2002 |
| CA | 2561210 | A1 | 10/2005 | WO | 02053516 A2 | 7/2002 |
| CA | 2562859 | A1 | 11/2005 | WO | 02/068420 A1 | 9/2002 |
| CA | 2576294 | A1 | 3/2006 | WO | 03/004496 A1 | 1/2003 |
| CA | 2590912 | A1 | 6/2006 | WO | 03000241 A2 | 1/2003 |
| CA | 2651089 | A1 | 11/2007 | WO | 03002531 A2 | 1/2003 |
| CN | 101234105 | A | 8/2008 | WO | 03004496 A1 | 1/2003 |
| DE | 2 205 815 | A1 | 8/1973 | WO | 03/024965 A2 | 3/2003 |
| DE | 2758025 | A1 | 7/1979 | WO | 03037327 A1 | 5/2003 |
| DE | 10109021 | A1 | 9/2002 | WO | 03/057200 A2 | 7/2003 |
| DE | 10117803 | A1 | 10/2002 | WO | 03055881 A1 | 7/2003 |
| DE | 10238243 | A1 | 3/2004 | WO | 03088900 A2 | 10/2003 |
| DE | 102004019540 | A1 | 11/2005 | WO | 03/104229 A1 | 12/2003 |
| DE | 102004024454 | A1 | 12/2005 | WO | 03099279 A1 | 12/2003 |
| DE | 102004044221 | A1 | 3/2006 | WO | 03099836 A1 | 12/2003 |
| DE | 102004054054 | A1 | 5/2006 | WO | 03106428 A1 | 12/2003 |
| EP | 0023032 | A1 | 1/1981 | WO | 2004011416 A1 | 2/2004 |
| EP | 0149578 | A2 | 7/1985 | WO | 2004/018467 A2 | 3/2004 |
| EP | 0223403 | A2 | 5/1987 | WO | 2004/018468 A2 | 3/2004 |
| EP | 0237608 | A1 | 9/1987 | WO | 2004/028524 A1 | 4/2004 |
| EP | 0248634 | A2 | 12/1987 | WO | 2004/033455 A2 | 4/2004 |
| EP | 0400974 | A2 | 5/1990 | WO | 2004/041820 A1 | 5/2004 |
| EP | 0 389 282 | A2 | 9/1990 | WO | 2004/046148 A1 | 6/2004 |
| EP | 0399285 | A1 | 11/1990 | WO | 2004/048379 A1 | 6/2004 |
| EP | 409281 | A1 | 1/1991 | WO | 2004/050658 A1 | 6/2004 |
| EP | 0412358 | A1 | 2/1991 | WO | 2004052362 A1 | 6/2004 |
| EP | 443983 | A1 | 8/1991 | WO | 2004062689 A1 | 7/2004 |
| EP | 0524482 | A1 | 1/1993 | WO | 2004065380 A | 8/2004 |
| EP | 0657454 | A1 | 6/1995 | WO | 2004081006 A1 | 9/2004 |
| EP | 0775704 | A1 | 5/1997 | WO | 2004/096806 A1 | 11/2004 |
| EP | 0950658 | A1 | 10/1999 | WO | 2004/108730 A1 | 12/2004 |
| EP | 1054012 | A1 | 11/2000 | WO | 2004/111051 A1 | 12/2004 |
| EP | 1333033 | | 8/2003 | WO | 2004106279 A2 | 12/2004 |
| EP | 1338595 | A2 | 8/2003 | WO | 2005000846 A1 | 1/2005 |
| EP | 1406873 | A2 | 4/2004 | WO | 2005000848 A1 | 1/2005 |
| EP | 1500403 | A1 | 1/2005 | WO | 2005012288 A1 | 2/2005 |
| EP | 1514552 | A1 | 3/2005 | WO | 2005023179 A2 | 3/2005 |
| EP | 1557165 | A1 | 7/2005 | WO | 2005/058901 A1 | 6/2005 |
| EP | 1537880 | A1 | 8/2005 | WO | 2005049022 A2 | 6/2005 |
| EP | 1586571 | A1 | 10/2005 | WO | 2005058901 A1 | 6/2005 |
| EP | 1760076 | | 3/2007 | WO | 2005061489 A1 | 7/2005 |
| EP | 1829877 | A1 | 9/2007 | WO | 2005/082906 A1 | 9/2005 |
| EP | 1852108 | A1 | 11/2007 | WO | 2005/085246 A1 | 9/2005 |
| ES | 385302 | A1 | 4/1973 | WO | 2005082906 A1 | 9/2005 |
| FR | 2707641 | A1 | 1/1995 | WO | 2005092870 A1 | 10/2005 |
| GB | 2084580 | A | 4/1982 | WO | 2005092877 A1 | 10/2005 |
| JP | S37-4895 | | 6/1962 | WO | 2005097798 A | 10/2005 |
| JP | 770120 | | 3/1995 | WO | 2005116000 A1 | 12/2005 |
| JP | 2001213770 | A | 8/2001 | WO | 2005116014 A1 | 12/2005 |
| JP | 2003/300977 | | 10/2003 | WO | 2005117861 A1 | 12/2005 |
| JP | 2006/045156 | | 2/2006 | WO | 2005117948 A1 | 12/2005 |
| KR | 20070111099 | A | 11/2007 | WO | 2006005613 A1 | 1/2006 |
| WO | 91/07945 | A1 | 6/1991 | WO | 2006/029769 A1 | 3/2006 |
| WO | 9107945 | A1 | 6/1991 | WO | 2006036664 A1 | 4/2006 |
| WO | 92/05175 | A1 | 4/1992 | WO | 2006040625 A1 | 4/2006 |
| WO | 94/02150 | A1 | 2/1994 | WO | 2006/048427 A1 | 5/2006 |
| WO | 94/03456 | A1 | 2/1994 | WO | 2006047248 A1 | 5/2006 |
| WO | 9609045 | A1 | 3/1996 | WO | 2006048209 A1 | 5/2006 |
| WO | 9636638 | A1 | 11/1996 | WO | 2006/068163 A1 | 6/2006 |
| WO | 97/23473 | A1 | 7/1997 | WO | 2006071078 A1 | 7/2006 |
| WO | 9723447 | A1 | 7/1997 | WO | 2006076231 A2 | 7/2006 |
| WO | 9746526 | A1 | 12/1997 | WO | 2006135693 A2 | 12/2006 |
| WO | 9807725 | | 2/1998 | WO | 2006137085 A1 | 12/2006 |
| WO | 9811893 | | 3/1998 | WO | 2007007173 A2 | 1/2007 |
| WO | 9822464 | A1 | 5/1998 | WO | 2007/017423 A2 | 2/2007 |
| WO | 9828007 | A1 | 7/1998 | WO | 2007014886 A1 | 2/2007 |
| WO | 9840069 | A2 | 9/1998 | WO | 2007014895 A2 | 2/2007 |
| WO | 9856406 | A1 | 12/1998 | WO | 2007033350 A1 | 3/2007 |
| WO | 99/29695 | A1 | 6/1999 | WO | 2007035355 A2 | 3/2007 |
| WO | 9950248 | A1 | 10/1999 | WO | 2007035665 A1 | 3/2007 |
| WO | 00/73307 | A2 | 12/2000 | WO | 2007041053 A2 | 4/2007 |
| WO | 0107441 | A1 | 2/2001 | WO | 2007071738 | 6/2007 |
| WO | 0152825 | | 7/2001 | WO | 2007072083 A1 | 6/2007 |
| WO | 0152852 | A1 | 7/2001 | WO | 2007078726 A2 | 7/2007 |
| WO | 0168646 | A1 | 9/2001 | WO | 2007093610 A1 | 8/2007 |

| | | | |
|---|---|---|---|
| WO | 2007099345 A1 | 9/2007 |
| WO | 2007120702 A2 | 10/2007 |
| WO | 2007120936 A2 | 10/2007 |
| WO | 2007128721 A | 11/2007 |
| WO | 2007128724 A1 | 11/2007 |
| WO | 2007128761 A2 | 11/2007 |
| WO | 2007135196 A2 | 11/2007 |
| WO | 2007137107 A2 | 11/2007 |
| WO | 2007148185 A2 | 12/2007 |
| WO | 2007149797 A2 | 12/2007 |
| WO | 2008/017670 A1 | 2/2008 |
| WO | 2008022267 A2 | 2/2008 |
| WO | 2008055870 A1 | 5/2008 |
| WO | 2008055940 A2 | 5/2008 |
| WO | 2008070692 A2 | 6/2008 |
| WO | 2008081205 A1 | 7/2008 |
| WO | 2008087198 A1 | 7/2008 |
| WO | 2008093878 A1 | 8/2008 |
| WO | 2008093882 A1 | 8/2008 |
| WO | 2008113000 A1 | 9/2008 |
| WO | 2008131149 A2 | 10/2008 |
| WO | 2009011451 A | 1/2009 |
| WO | 2009022007 A1 | 2/2009 |
| WO | 2009022008 A1 | 2/2009 |
| WO | 2009022010 A1 | 2/2009 |
| WO | 2009024542 A2 | 2/2009 |
| WO | 2009063072 A2 | 5/2009 |
| WO | 2009099734 A1 | 8/2009 |
| WO | 2009121945 A2 | 10/2009 |
| WO | 2009123992 A1 | 10/2009 |
| WO | 2009147125 A1 | 12/2009 |
| WO | 2010015664 A1 | 2/2010 |
| WO | 2010018217 A2 | 2/2010 |
| WO | 2010029089 A2 | 3/2010 |
| WO | 2010043688 A1 | 4/2010 |
| WO | 2010045656 A2 | 4/2010 |
| WO | 2010072776 A1 | 7/2010 |
| WO | 2010079197 A1 | 7/2010 |
| WO | 2010086411 A1 | 8/2010 |
| WO | 2010092125 A1 | 8/2010 |
| WO | 2010092163 A2 | 8/2010 |
| WO | 2010106457 A2 | 9/2010 |
| WO | 2010147768 A1 | 12/2010 |
| WO | 2011039367 A2 | 4/2011 |
| WO | 2011064352 A1 | 6/2011 |
| WO | 2011113947 A1 | 9/2011 |
| WO | 2011138380 A1 | 11/2011 |
| WO | 2011138421 A1 | 11/2011 |
| WO | 2011161161 A1 | 12/2011 |
| WO | 2012065993 A1 | 5/2012 |

OTHER PUBLICATIONS

Bastin, et al., Salt Selection and Optimisation Procedures for Pharmaceutical New Chemical Entitites, vol. 4, Organic Process Research & Development, pp. 427-435, 2000.*

Yoshikawa, Seiji et al.: Chemical Abstract of Japanese Patent No. WO 2003/104229 Preparation of purinone derivatives as dipeptidylpeptidase IV (DPP-IV) inhibitors.

Patani George A. et al.: "Bioisoterism : A Rational Approach in Drug Design", Chemical Reviews, 1996, vol. 96, No. 8, pp. 3147-3176.

Priimenko, B. A., et al; Synthesis and Pharmacological Activity of Derivatives of 6,8-Dimethyl Imidazo(1,2-f)Xanthine-(Russ.); Khimiko-Farmatsevticheskii Zhurnal (1984) vol. 18, No. 12 pp. 1456-1461.

Salomon, J., et al; Ultraviolet and γ-Ray-Induced reactions of Nucleic Acid Constituents. Reactions of Purines With Amines; Photochemistry and Photobiology (1974) vol. 19 pp. 21-27.

International Search Report for PCT/EP2005/055711 dated Mar. 29, 2006.

U.S. Appl. No. 11/744,701, filed May 4, 2007, Kohlrausch, Unpublished.

Augustyns, K. et al., The Unique Properties of Dipeptidyl-peptidase IV (DPP IV/CD 26) and the Therapeutic Potential of DPP-IV Inhibitors, Current Medicinal Chemistry, vol. 6, No. 4, 1999, pp. 311-327.

Beljean-Leymarie et al., Hydrazines et hydrazones hétérocycliques. IV. Synthèses de dérivés de l'hydrazine dans la série des imidazo[4,5-d]pyridazinones-4, Can. J. Chem., vol. 61, No. 11, 1983, pp. 2563-2566.

Bollag, R.J. et al; "Osteoblast-Derived Cells Express Functional Glucose-Dependent Insulinotropic Peptide Receptors," Endocrinology, vol. 141, No. 3, 2000, pp. 1228-1235.

Brittain, H.G., "Methods for the Characterization of Polymorphs: X-Ray Powder Diffraction," Polymorphism in Pharmaceutical Solids, 1999, p. 235-238.

Busso et al., "Circulating CD26 is Negatively Associated with Inflammation in Human and Experimental Arthritis," Am. J. Path., vol. 166, No. 2, Feb. 2005, pp. 433-442.

Caira, M.R., "Crystalline polymorphism of organic compounds" Topics in Current Chemistry, Springer, Berlin, vol. 198, 1998, p. 163-208.

Chemical Abstracts Accession No. 1987:95577: Abstract of Romanenko et al., "Synthesis and biological activity of 3-methyl, 7- or 8-alkyl, 7,8-dialkyl, heterocyclic, and cyclohexylaminoxanthines," Farmatsevtichnii Zhurnal, 1986, (Kiev), vol. 5, 1986, pp. 41-44.

Chemical Abstracts Accession No. 106:95577 Romanenko et al., "Synthesis and biological activity of 3-methyl, 7-or 8-alkyl-7,8-dialkyl, heterocyclic, and cyclohexylaminoxanthines," Zaporozh. Med. Institute (1986).

Conarello, S.L. et al; "Mice lacking dipeptidyl peptidase IV are protected against obesity and insulin resistance," PNAS 2003; 100:6825-6830; originally published online May 14, 2003; information current as of Dec. 2006. www.pnas.org/cgi/content/full/100/11/6825.

Cygankiewicz, Andrzej et al., Investigations into the Piperazine Derivatives of Dimethylxanthine:, Acta Polon. Pharm. [Papers of Polish Pharmacology], XXXOV, No. 5, pp. 607-612, 1977.

Deacon, C.F. et al; "Dipeptidyl peptidase IV inhabitation as an approach to the treatment and prevention of type 2 diabetes: a historical perspective;" Biochemical and Biophysical Research Communications (BBRC) 294 (2002) 1-4.

DeMeester, I. et al.; "CD26, let it cut or cut it down", Review: Immunology Today; Aug. 1999, vol. 20, No. 8 pp. 367-375.

Januvia; Patient Information; Oct. 2007.

Korom, S. et al; Inhibition of CD26/dipeptidyl peptidase IV activity in vivo prolongs cardiac allograft survival in rat recipients, Transplantation, May 27, 1997, vol. 63, No. 10, pp. 1495-1500.

Pospisilik, et al; Dipeptidyl Peptidase IV Inhibitor Treatment Stimulates β-Cell Survival and Islet Neogenesis in Streptozotocin-Induced Diabetic Rats; Diabetes, vol. 52, Mar. 2003 pp. 741-750.

Rhee et al.: "Nitrogen-15-Labeled Deoxynucleosides. 3. Synthesis of [3-$^{15}$N]-2'-Deoxyadenosine" J. Am. Chem. Soc. 1990, 112, 8174-8175.

Sedo, A. et al; "Dipeptidyl peptidase IV activity and/or structure homologs: Contributing factors in the pathogenesis of rheumatoid arthritis?" Arthritis Research & Therapy 2005, vol. 7, pp. 253-269.

Tanaka, S.. et al; "Suppression of Arthritis by the Inhibitors of Dipeptidyl Peptidase IV," in. J. Immunopharmac., vol. 19, No. 1, pp. 15-24, 1997.

Wolff, M.E.: "Burger's Medicinal Chemistry and Drug Discovery" Fifth Edition, vol. 1: Principles and Practice, pp. 975-977, 1994, John Wiley & Sons, Inc.

Zejc, Alfred et al; "Badania Nad Piperazynowymi Pochodnymi Dwumetyloksantyn" Acta Polon Pharm, XXXV, Nr. 4, 1976, pp. 417-421.

Zhong, Qing et al; "Glucose-dependent insulinotropic peptide stimulates proliferation and TGF-β release from MG-63 cells," Peptides 24 (2003) 611-616.

International Search Report for PCT/EP03/09127 mailed Nov. 28, 2003.

International Search Report for PCT/EP03/12821 mailed Mar. 30, 2004.

International Search Report for PCT/EP03/13648 mailed Apr. 5, 2004.

International Search Report for PCT/EP2007/054270 mailed Aug. 14, 2007.

International Search Report for PCT/EP2007/058181 mailed Nov. 28, 2007.

International Search Report for PCT/EP2007/054204 mailed Aug. 3, 2007.

International Search Report for PCT/EP2007/054201 mailed Aug. 29, 2007.

Clinical Trials: NCT00954447, View on Jun. 14, 2010. "Efficacy and Safety of Linagliptin in Combination with Insulin in Patients with Type 2 Diabetes". <http://clinicaltrials.gov/archive/NCT00954447/2010_06_14>.

Jones, R.M. et al., "GPR119 agonists for the treatment of type 2 diabetes". Expert Opinion on Therapeutic Patents 2009 Informa Healthcare for GBR LNKSD—DOI: 10.1517/13543770903153878, vol. 19, No. 10, Oct. 2009, p. 1339-1359.

Meece, J. "When Oral Agents Fail: Optimizing Insulin Therapy in the Older Adult". Consultant Pharmacist, The Society, Arlington, VA US. vol. 24, No. Suppl B, Jun. 1, 2009, p. 11-17.

Rosenstock, J. et al., "Alogliptin added to insulin therapy in patients with type 2 diabetes reduces HbA1c without causing weight gain or increased hypoglycaemia". Diabetes, Obesity and Metabolishm, Dec. 2009, vol. 11. No. 12, p. 1145-1152.

Sune Negre, J. M. "New Galenic Contributions to Administration Forms". Continued Training for Hospital Pharmacists 3.2. No date available for this reference. http://www.ub.es/legmh/capitols/sunyenegre.pdf.

Thomas, L., "Chronic treatment with the Dipeptidyl Peptidase-4 Inhibitor BI 1356[9R)-8-(3-Amino-piperidin-1-yl)-7-but-2-ynyl-3-methyl-1(4-methyl-quinazolin-2-ylmethyl)-3,7-dihydro-purine-2,6-dione] Increases Basal Glucagon-Like Peptide-1 and Improves Glycemic Control in Diabetic Rodent Models" The Journal of Pharmacology and Experimental Therapeutics, Feb 2009, vol. 328, No. 2, pp. 556-563.

Abstract in English for German DE2205815, 1972.

Abstract in English for German EP0023032, 1981.

Abstract in English, for KR20070111099, Nov. 11, 2007.

Ahren B: "DPP-4 inhibitors", Best practice and research in clinical endocrinology and metabolism—New therapies for diabetes 200712 GB LNKD—DOI:10.1016/J. Beem.2007.07.005, vol. 21, No. 4, Dec. 2007, pp. 517-533.

Augeri, D.J. "Discovery and Preclinical Profile of Saxagliptin (GMB-477118): A Highly Potent, Long-Acting, Orally Active Dipeptidyl Peptidase IV Inhibitor for the Treatment of Type 2 Diabetes". Journal Med. Chem, 2005, vol. 48, No. 15, p. 5025-5037.

Aulinger, B.A. et al., "Ex-4 and the DPP-IV Inhibitor Vildagliptin have Additive Effects to Suppress Food Intake in Rodents". Abstract No. 1545-P, 2008.

Balaban, Y.H.et al., "Dipeptidyl peptidase IV (DDP IV) in NASH patients" Annals of Hepatology, vol. 6, No. 4, Oct. 1, 2007, pp. 242-250, abstract.

Balkan, B. et al, "Inhibition of dipeptidyl peptidase IV with NVP-DPP728 increases plasma GLP-1 (7-36 amide) concentrations and improves oral glucose tolerance in obses Zucker rates". Diabetologia, 1999, 42, p. 1324-1331.

Brazg, R. et al: "Effect of adding sitagliptin, a dipeptidyll peptidase-4 inhibitor, to metformin on 24-h glycaemic control and beta-cell function in patients with type 2 diabetes." Diabetes, Obesity and Metabolism, Mar. 2007, vol. 9, No. 2, Mar. 2007 pp. 18-193.

Bundgaard, H. "Design of prodrugs: Bioreversible derivatives for various functional groups and chemical entities". Royal Danish School of Pharmacy, 1985, p. 1-92.

Chemical Abstract. EP412358, 1991:185517, Findeisen.

Chemical Abstract: FR2707641, 1995:543545, Dodey.

Chemical Abstracts Accession No. 106:95577 Romanenko et al., "Synthesis and Biological Activity of 3-Methyl, 7- or 8-alkyl-7,8dialkyl, heterocyclic, and cyclohexylaminoxanthines," Zaporozh. Med. Institute (1986).

Clinical Trials. "View of NCT00601250 on Jan. 25, 2008: Efficacy and Safety of BI 1356 vs Placebo added to Metformin Background Therapy in Patients with Type 2 Diabetes" Clinical Trials. Gov Archive, [Online] Jan. 25, 2008 URL:http://clinicaltrials.gov/archive/NCTO0601250/2008_01_25 [retrieved on Feb. 27, 2009].

Clinical Trials. NCTO0622284. "Efficacy and safety of BI 1356 in combination with metformin in patients with type 2.diabetes" ClinicalTrials.gov (Online) No. NCT00622284, Feb. 13, 2008, p. 1-5, URL:http://clinicaltrial.gov/ct2/show/.

Clinical Trials. View of NCT00730275 updated on Aug. 7, 2008. "A study to assess the pharmacokinetics, safety and tolerability of Sitagliptin in adolescents". http://clinicaltrials.gov/archive/NCT00730275/2008_08_07.

Clinical Trials: NCT00309608. Efficacy and safety of BI 1356 in combination with metformin in patients with type2 diabetes. Boehringer Ingelheim Pharmaceuticals, Jan. 27, 2009. Clinical Trials.gov . http://clinicaltrials.gov/archive/NCT00309608/2009_01_27.

Clinical Trials: NCT00602472. "BI 1356 in combination withe metformin and a sulphonylurea in Type 2 Diabetes". DrugLib.com, Nov. 3, 2008. http://www.druglib.com/trial/08/NCT00309608.html.

Clinical Trials: NCT00622284. Efficacy and Safety of BI 1356 in Combination with Metformin in Patients with Type 2 Diabetes. Boehringer Ingelheim Pharmaceuticals, Aug. 2008. http://clinicaltrials.gov/archive/NCT00622284/2010_01_13.

Clinical Trials: NCT00798161. "Safety and efficacy of Bi 1356 Plus Metformin in Type 2 Diabetes, Factorial Design". Clinical Trials.gov archive. A Service of the U.S> National Institutes of Health. Nov. 24, 2008, p.1-3. http://clinicaltrials.gov/archive/NCT00798161/2008_11_24.

Combs, D. W. et al., "Phosphoryl Chloride Induced Ring Contraction of 11,4-Benzodiazepinones to Chloromethylquinazolines". J. Heterocyclic Chemistry, BD. 23, 1986, p. 1263-1264.

Dave, K.G. et al., "Reaction of Nitriles under Acidic Conditions, Part I. A General Method of Synthesis of Condensed Pyrimidines", J. Heterocyclic Chemistry, BD, 17, 1, ISSN 0022-152X,Nov. 1980, p. 1497-1500.

Deacon, C.F., et al. Inhibitors of dipeptidyl peptidase IV: a novel approach for the prevention and treatment of Type 2 diabetes? Expert Opinion on Investigational Drugs, 2004, Sep., vol. 13, No. 9, p. 1091-1102.

Dugi, K.A. et al., "BI 1356, a novel xanthine-based DPP-IV inhibitor, exhibits high potency with a wide therapeutic window and significantly reduces postprandial glucose excursions after an oGTT". Diabetologia, vol. 50, No. Suppl 1, Sep. 2007, p. S367, and 43rd Annual Meeting of the European Association for the Study of Diabetes; Amsterdam, Netherlands, Sep. 18-21, 2007.

Eckhardt Matthias et al: 8-(3-(R)-aminopiperidin-1-yl)-7-but-2-yny 1-3-methyl-1-(4-methyl-quina zolin-2-ylmethyl)-3,7-dihydropurine-2,6-dione (BI 1356), a highly potent, selective, long-acting, and orally bioavailable DPP-4 inhibitor for the treatment of type 2 diabetes: Journal of Medicinal Chemistry, American Chemical Society. Washington.; US, vol. 50, No. 26, Dec. 1, 2007, p. 6450-6453.

Eckhardt, M. et al., "3,5-dihydro-imidazo[4,5-d]pyridazin-4-ones: a class of potent DPP-4 inhibitors" Bioorganic & Medicinal Chemistry Letters, Pergamon, Elsevier Science, GB, vol. 18, No. 11, Jun. 1, 2008, pp. 3158-3162, XP022711188.

Elrishi M a et al: "The dipeptidyl-peptidase-4 (D::-4) inhibitors: A new class of oral therapy for patients with type 2 diabetes mellitus" Practical Diabetes International Chichester, vol. 24, No. 9, Nov. 1, 2007 pp. 474-482.

Florez, Jose C., et al., "TCF7L2 Polymorphisms and progression to diabetes in the diabetes prevention program". New England Journal of Medicine, MA Medical Society, vol. 355, No. 2, Jul. 20, 2006, p. 241-250.

Gallwitz, B. et al., "Saxagliptin, a dipeptidyl peptidase IV inhibitor for the treatment of type 2 diabetes". Drugs, vol. 11, No. 12, Dec. 2008, p. 906-917.

Garber, A.J. et al., "Update: Vildaglitin for the treatment of Type 2 diabetes" Expert Opinion on Investigational Drugs, 200801GB, vol. 17, No. 1, Jan. 2008, p. 105-113.

Garcia-Soria, et al., "The dipeptidyl peptidase-4 inhibitor PHX1149 improves blood glucose control in patents with type 2 diabetes mellitus". Diabetes, Obesity and Metabolism, Apr. 2008, vol. 10, No. 4, p. 293-300.

Gennaro, Alfonso, R; Remington: The Science and Practice of Pharmacy: Oral Solid Dosage Forms; Mack Publishing Company, Philadelphia, PA (1995) vol. II, 19th Edition, Ch. 92 pp. 1615-1649.

Giron, D.; Thermal Analysis and Calorimetric Methods in the Characterisation of Polymorphs and Solvates; Thermochimica Acta (1995) vol. 248 pp. 1-59.

Graefe-Mody et al., "The novel DPP-4 inhibitor " Diabetes, (online) 2008, XP002561421 http://professional.diabetes.org/content/posters/2008/p553-p.pdf.

Greene, T.W, et al., "Protection for the Amino Group". Protective Groups in Organic Synthesis, 3rd edition, 1999, p. 494-653.

Gwaltney, S. "Medicinal Chemistry Approaches to the Inhibition of Dipeptidyl Peptidase IV", Current Topics in Medicinal Chemistry, 2008, 8, p. 1545-1552.

He, Y.L. et al., "The influence of hepatic impairment on the pharmacokinetics f the dipeptidyl peptidase IV (DPP-4) inhibitor vidagliptin" European Journal of Clinical Pharmacology, vol. 63, No. 7, May 8, 2007, p. 677-686.

Huettner Silks et al: "BI 1356, a novel and selective xanthine based DPP-IV inhibitor, demonstrates good safety and tolerability with a wide therapeutic window" Diabetes< American Diabetes Association, US, vol. 56, No. Suppl 1, Jun. 1, 2007, p. A156.

International Search Report and Written Opinion for PCT/EP2011/057163 mailed Jun. 27, 2011.

Kanada, S. et al., "Safety, tolerability, pharmacokenetics and pharmacodynamics of multiple doses of BI 1356 (proposed tradename Ondero), a dipeptidyl peptidase 4 inhibitor, in Japanese patients with type 2 diabetes" Diabetes, vol. 57, No. Suppl. 1, Jun. 2008, p. A158-A159 and 68th Annual Meeting of the American Diabetes Association: San Francisco, CA , Jun. 6-10, 2008.

Kim, D. et al., "(2R)-4-0xo-4-(3-(Trifluoremethyl)-5,6-dihydro[1,2,4]triazolo[4,3-a]pyrazin-7(8H)-yl-1-(2,4,5-trifluorophenyl)butan-2-amine: A Potent, Orally Active Dipeptidyl Peptidase IV inhibitor for the Treatment of Type 2 Diabetes." Journal Med. Chem, 2005, 48, p. 141-151.

Lambier, A.M. et al., Dipeptidyl-Peptidase IV from Bench to Bedside: An Update on Structural Properties, Functions, and Clinical Aspects of the Enzyme DPP IV. Critical Reviews in Clinical Laboratory Sciences, 2003, 40(3), p. 209-294.

March, J. "Advanced Organic Chemistry: Reactions, Mechanisms, and Structure". Fourth Edition, 1992, pp. 652-653.

Mendes, F.D, et al. "Recent advances in the treatment of non-alcoholic fatty liver disease". Expert Opinion on Investigational Drugs, vol. 14, No. 1, Jan. 1, 2005, p. 29-35.

Merck: "Initial Therapy with Janumet (sitagliptin/metformin) provided significantly greater blood sugar lowering compared to metformin alone in patients with type 2 diabetes". Webwire.com, Jun. 8, 2009, p. 1-4. http://www.webwire.com/ViewPressRel.asp?ald=96695.

O'Farrell, et al., "Pharmacokinetic and Pharmacodynamic Assessments of the Dipeptidyl Peptidase-4 Inhibitor PHX1149: Double-Blind, Placebo-controlled, Single-and Multiple-Dose Studies in Healthy Subjects". Clinical Therapeutics, Excerpta Medica, Princeton, NJ, vol. 29, No. 8, 2007, p. 1692-1705.

Pei, Z.: "From the bench to the bedside: Dipeptidyl peptidase IV inhibitors, a new class of oral antihyperglycemic agents" Current Opinion in Drug Discovery and Development, Current Drugs, London, GB vol. 11, No. 4, Jul. 1, 2008 pp. 512-532.

Rosenstock, et al., "Efficacy and tolerability of initial combination therapy with vildagliptin and pioglitazone compared with component montherapy in patients with type 2 diabetes". Diabetes, Obesity and Metabolism, Mar. 2007, vol. 9, No. 2, p. 175-185.

Sathananthan, A., et al., "Personalized pharmacotherapy for type 2 diabetes mellitus". Personalized Medicine 2009 Future Medicine Ltd, vol. 6, No. 4, Jul. 2009, p. 417-422.

Sauer, R, et al. "Water-soluble phosphate prodrugs of 1-Propargyl-7-styrylxanthine derivatives, A2A-selective adenosine receptor antagonists". Journal Med. Chem., vol. 43, Issue 3, Jan. 2000, p. 440-448.

Schwartz, M. S. et al., "Type 2 Diabetes Mellitus in Childhood: Obesity and Insulin Resistance". JAOA Review Article, vol. 108, No. 9, Sep. 2008, p. 518.

Scientific Discussion: "Eucreas. Scientific discussion". Online Oct. 2007, p. 1-27, URL:http://www.emea.europa.eu/humandocs/PDFs/EPAR/eucreas/H-807-en6.pdf. see point 2. quality aspects pp. 2-4. (EMEA).

Stahl, P.H., "Handbook of Pharmaceutical Salts". C.G. Wermuth, Wiley-VCH, 2002, p. 61.

Tamm, E, et al., "Double-blind study comparing the immunogenicity of a licensed DTwPHib-CRM197 conjugate vaccine (Quattvaxem TM) with three investigational, liquid formulations using lower doses of Hib-CRM197 conjugate". Science Direct, Vaccine, Feb. 2005, vol. 23, No. 14, p. 1715-1719.

Thomas, L, et al: "BI 1356, a novel and selective xanthine beased DPP-IV inhibitor, exhibits a superior profile when compared to sitagliptin and vildagliptin." Diabetologoa, vol. 50, No. Suppl. 1, Sep. 2007, p. S363.

Thomas, Leo et al: "(R)-8-(3-Amino-piperidin-l-yl)-7-but-2-ynyl-3-methyl-1- (4-methyl-quinazolin-2-ylmethyl)-3,7- dihydro-purine-2,6-dione (BI 1356), a Novel Xanthine-Based Dipeptidyl Peptidase 4 Inhibitor, Has a Superior Potency and Longer Duration of Action Compared with Other Dipeptidyl Peptidase-4 Inhibitors" Journal of Pharmacology and Experimental Therapeutics, American Socity for Therapeutics, US, vol. 325, No. 1, Apr. 1, 2008, pp. 175-182 abstract p. 177, col. 2, paragraph 1 table 1 p. 1B1, col. 2, last paragraph-p. 182, col. 1.

U.S. Appl. No. 12/724,653, filed Mar. 16, 2010—Xanthine Derivatives, the Preparation Thereof and Their Use as Pharmaceutical Compositions. Inventor: Frank Himmelsbach, et al.

U.S. Appl. No. 12/767,855, filed Apr. 27, 2010—Xanthine Derivatives, the Preparation Thereof and Their use as Pharmaceutical Compositions. Inventor: Frank Himmelsbach, et al.

Villhauer, E.B., "1-[[3-Hydroxy-1-adamantypamino]acetyl]-1-cyano-(S)-pyrrolidine: A Potent, Selective, and Orally Bioavailable Dipeptidyl Peptidase IV Inhibitor with Antihyperglycemic Properties" Journal Med. Chem, 2003, 46, p. 2774-2789.

Villhauer, E.B., et al., "1-{2-{5-Cyanopyridin-2-yl)amino}-ethylamino}acetyl-1-1(S)-pyrrolidine-carbonitrile: A Potent, Selective, and Orally Bioavailable Dipeptidyl Peptidase IV Inhibitor with Antihyperglycemic Properties". Journal of Medical Chemistry, 2002, vol. 45, No. 12, p. 2362-2365.

Wang Y et al: "BI-1356. Dipeptidyl-peptidase IV inhibitor, antidiabetic agent" Drugs of the Future, Prous Science, ES,vol. 33, No. 6, Jun. 1, 2008, pp. 473-477.

White, J.R., "Dipeptidyl Peptidase-IV Inhibitors: Phamacological Profile and Clinical Use". Clinical Diabetes, vol. 26, 2008, p. 53-57.

Wikipedia, Annulation. Jun. 23, 2008, http://en.wikipedia.org/wiki/Annelation.

Williams-Herman, D. et al., "Efficacy and safety of initial combination therapy with sitagliptin and metformin in patients with type 2 diabetes: a 54-week study". Current Medical Research and Opinion, Informa Healthcare, GB, vol. 25, No. 3, Jan. 2009, p. 569-583.

World Health Organization (WHO). "Addendum 1 to "The use of stems in the selection of International Nonproprietary names (INN) for pharmaceutical substances"" Online Jun. 19, 2007, pp. 1-3, retrieved from URL: http://www.who.int/medicindedocs/index/assoc/s1414e/s1414e.pdf.

X-Ray Diffraction. The United States Pharmacopeia, 2002, USP 25 NF20, p. 2088-2089.

Yasuda, et al. "E3024 3-but-2-ynyl-5-methyl-2-piperazin-1-y1-3,5-dihydro-4H-imidazol [ 4,5-d]pyridazin-4-one tosylate, is a move, selective and competitive dipeptidyl peptidase-IV inhibitor". European Journal of Pharmacology, vol. 548, No. 1-3, Oct. 24, 2006, p. 181-187. Abstract.

Zimmer et al; Synthesis of 8-Substituted Xanthines and their Oxidative Skeleton Rearrangement to 1-Oxo-2,4,7,9-tetraazaspiro[4,5]dec-2-ene-6,8,10-triones; Euripean Journal Organic Chemistry (1999) vol. 9 pp. 2419-2428.

He, Y. L. et al., "Bioequivalence of Vildagliptin/Metformin Combination Tablets and Coadministration of Vildagliptin and Metformin as Free Combination in Healthy Subjects". J. Clinical Pharmacology, 2007, vol. 47, No. 9, Abstracts of the 36th Annual Meeting of the American College of Clinical Pharmacology, San Francisco, CA, Abstract 116, p. 1210.

Sune Negre, J. M. "New Galenic Contributions to Administration Forms". Continued Training for Hospital Pharmacists 3.2. [retrieved on Feb. 23, 2011] . Retrieved from the internet <http://www.ub.es/legmh/capitols/sunyenegre.pdf>.

Knorr, M. et al., "Comparison of Direct and Indirect Antioxidant Effects of Linagliptin (BI 1356, Ondero) with other Gliptins—Evidence for Anti-Inflammatory Properties of Linagliptin". Free Radical Biology and medicine, Elsevier Science, U.S. vol. 49, Oct. 23, 2010, p. S197.

International Search Report and Written Opinion for PCT/EP2010/064691 mailed Apr. 6, 2011.

Demuth, H-U. et al., "Type 2 diabetes—Therapy with dipeptidyl peptidase IV inhibitors". Biochimica et Biophysica Acta, vol. 1751(1), 2005, p. 33-44.

Hunziker, D. et al, "Inhibitors of DPP IV-recent advances and structural views", Current Topics in Medicinal Chemistry, 2005, vol. 5 issue 16, pp. 1623-1637.

Conarello, S.L. et al; "Mice lacking dipeptidyl peptidase IV are protected against obesity and insulin resistance," PNAS 2003; 100:6825-6830; originally published online May 14, 2003; information current as of Dec. 2006. www.pnas.org/cgi/content/full/100/11/6825.

Gallwitz, B. "Sitagliptin with Metformin: Profile of a Combination for the Treatment of Type 2 Diabetes". Drugs of Today, Oct. 2007, 43(10), p. 681-689.

Graefe-Mody, et al; Evaluation of the Potential for Steady-State Pharmacokinetic and Phamacodynamic Interactions Between the DPP-4 Inhibitor Linagliptin and Metformin in Healthy Subjects; Currents Medical Research and Opinion (2009) vol. 25, No. 8 pp. 1963-1972.

Uhlig-Laske, B. et al., "Linagliptin, a Potent and Selective DPP-4 Inhibitior, is Safe and Efficacious in Patients with Inadequately Controlled Type 2 Diabetes Despite Metformin Therapy". 535-P Clinical Therapeutics/New Technology—Pharmacologic Treatment of Diabetes or Its Complications, Posters, vol. 58, Jun. 5, 2009, p. A143.

Jones, R.M. et al., "GPR119 agonists for the treatment of type 2 diabetes". Expert Opinion on Therapeutic Patents 2009 Informa Healthcare for GBR LNKSD—DOI: 10.1517/13543770903153878, vol. 19, No. 10, Oct. 2009, p1339-1359.

Levien,T.L. et al, "New drugs in development for the treatment of diabetes", Diabetes Spectrum, American Diabetes Association, US, vol. 22, No. 2, Jan. 1, 2009, pp. 92-106.

Meece, J. "When Oral Agents Fail: Optimizing Insulin Therapy in the Older Adult". Consultant Pharmacist, The Society, Arlington, VA US. vol. 24, No. Suppl B, Jun. 1, 2009, p11-17.

Rosenstock, J. et al., "Alogliptin added to insulin therapy in patients with type 2 diabetes reduces HbA1c without causing weight gain or increased hypoglycaemia". Diabetes, Obesity and Metabolishm, Dec. 2009, vol. 11. No. 12, p1145-1152.

Sune Negre, J. M. "New Galenic Contributions to Administration Forms". Continued Training for Hospital Pharmacists 3.2. No date available for this reference. http://www.ub.es.legmh/capitols/suntenegre.pdf, date filed: Oct. 25, 2011.

Oct. 25, 2011. Thomas, L., "Chronic treatment with the Dipeptidyl Peptidase-4 Inhibitor Bi 1356[9R)-8-(3-Amino-piperidin-1-yl)-7-but-2-yny1-3-methyl-1(4-methyl-quinazolin-2-ylmethyl)-3,7-dihydro-purine-2,6-dione] Increases Basal Glucagon-Like Peptide-1 and Improves Glycemic Control in Diabetic Rodent Models" The Journal of Pharmacology and Experimental Therapeutics, Feb. 2009, vol. 328, No. 2, pp. 556-563.

\* cited by examiner

PROCESS FOR THE PREPARATION OF CHIRAL 8-(3-AMINOPIPERIDIN-1YL)-XANTHINES

This application is a divisional of U.S. patent application Ser. No. 11/267,235 filed Nov. 4, 2005, the content of which is hereby incorporated by reference in its entirety.

The invention relates to an improved process for preparing chiral 8-(3-aminopiperidin-1-yl)-xanthines, their enantiomers and their physiologically tolerated salts.

8-(3-aminopiperidin-1-yl)-xanthines of the following general structure

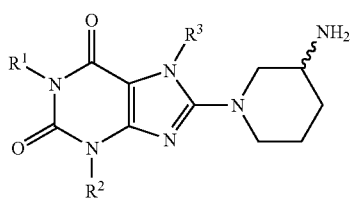

(I)

in which $R^1$ is, for example, an optionally substituted arylmethyl group or an optionally substituted heteroarylmethyl group, $R^2$ is, for example, an alkyl group and $R^3$ is, for example, an optionally substituted benzyl group or a straight-chain or branched alkenyl or alkinyl group are already known from the international applications WO 02/068420, WO 04/018468, WO 04/018467, WO 2004/041820 and WO 2004/046148, in which compounds having valuable pharmacological properties are described, which include in particular an inhibiting action on the activity of the enzyme dipeptidylpeptidase IV (DPP-IV). Therefore, compounds of this type are suitable for preventing or treating disorders or states which are connected with an increased DPP-IV activity or which can be prevented or alleviated by reduction in the DPP-IV activity, especially of diabetes mellitus type I or type II, prediabetes, or reduction of glucose tolerance.

WO 04/018468 discloses a preparation process in which 8-(3-aminopiperidin-1-yl)-xanthines are prepared by deprotecting a corresponding tert.-butyloxycarbonyl-protected derivative of the general formula (II).

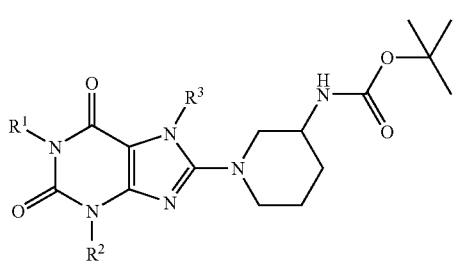

(II)

In this process, impurities which were difficult to remove, especially on the industrial scale, occurred, and are attributable to the protecting group used. The process was therefore unsuitable for the industrial preparation of 8-(3-aminopiperidin-1-yl)-xanthines, especially for medicament production with its strict demands on purity. Furthermore, the method had the disadvantage that the preparation of the enantiomerically pure precursor 3-(tert.-butyloxycarbonylamino)piperidine is complicated and expensive. However, enantiomerically pure active ingredients are to be preferred for the pharmaceutical application owing to the risk of side effects and for the reduction of the dose to a minimum. These circumstances count against the suitability of the known process for the industrial preparation of enantiomerically pure 8-(3-aminopiperidin-1-yl)-xanthines.

In the light of the above-described disadvantages of the known preparation process, it is an object of the present invention to provide a process which allows the preparation of enantiomerically pure 8-(3-aminopiperidin-1-yl)-xanthines using readily obtainable starting materials in high chemical and optical purity and without great technical cost and inconvenience. This novel process should also be suitable for synthesis on the industrial scale and thus for commercial application.

This object is achieved by the process according to the invention for preparing chiral 8-(3-aminopiperidin-1-yl)-xanthines. In addition to high yield industrial performance, very good chemical and optical purities are further advantages of the inventive synthetic route.

According to the process of the present invention, the appropriate xanthine precursor (III) is reacted according to scheme 1 with enantiomerically pure or racemic 3-(phthalimido)piperidine in suitable solvents at temperatures of 20 to 160° C.; preferably of 8 to 140° C. The solvents used may, for example, be tetrahydrofuran (THF), dioxane, N,N-dimethylformamide (DMF), dimethylacetamide (DMA), N-methyl-2-pyrrolidone (NMP) or dimethyl sulphoxide (DMSO). Preference is given to using NMP. Subsequently, the phthalyl protecting group is detached by processes known per se. Possible detachment methods are described, for example, by T. W. Greene in "Protective Groups in Organic Synthesis", Wiley 1981 on page 265 (for example hydrazine in ethanol).

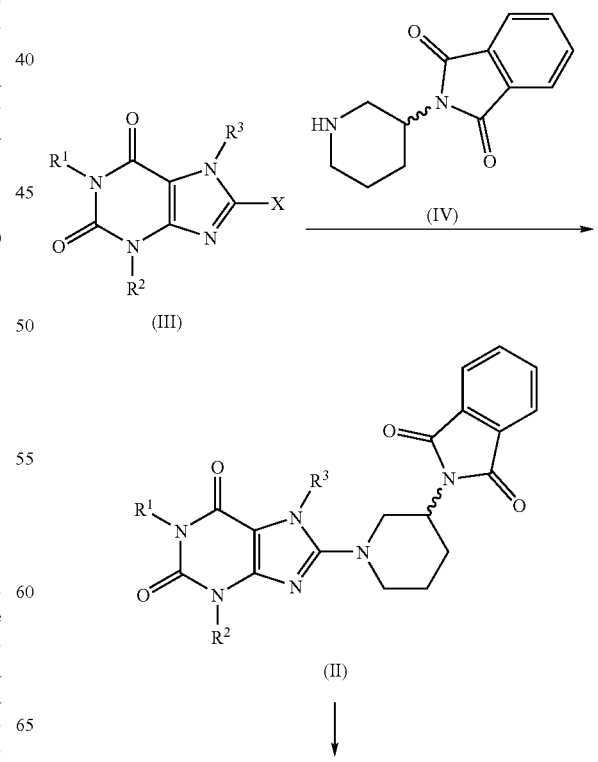

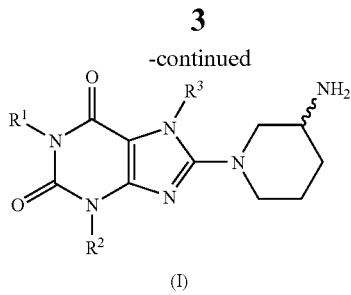

(I)

In the abovementioned formulae,
X is a leaving group selected from the group of the halogens, for example a fluorine, chlorine or bromine atom, or of the sulphonic esters, for example a phenylsulphonyloxy, p-toluenesulphonyloxy, methylsulphonyloxy or trifluoromethylsulphonyloxy group,
$R^1$ is a phenylcarbonylmethyl, benzyl, naphthylmethyl, pyridinylmethyl, pyrimidinylmethyl, quinolinylmethyl, isoquinolinylmethyl, quinazolinylmethyl, quinoxalinylmethyl, naphthyridinylmethyl or phenanthridinylmethyl group in which the aromatic or heteroaromatic moiety is in each case mono- or disubstituted by $R_a$, where the substituents may be identical or different and $R_a$ is a hydrogen, fluorine, chlorine or bromine atom or a cyano, methyl, trifluoromethyl, ethyl, phenyl, methoxy, difluoromethoxy, trifluoromethoxy or ethoxy group, or two $R_a$ radicals, when they are bonded to adjacent carbon atoms, may also be an —O—CH$_2$—O— or —O—CH$_2$—CH$_2$—O— group, $R^2$ is a methyl, ethyl, propyl, isopropyl, cyclopropyl or phenyl group and
$R^3$ is a 2-buten-1-yl, 3-methyl-2-buten-1-yl, 2-butin-1-yl, 2-fluorobenzyl, 2-chlorobenzyl, 2-bromobenzyl, 2-iodobenzyl, 2-methylbenzyl, 2-(trifluoromethyl)benzyl or 2-cyanobenzyl group.

The process is preferable for those compounds in which
X is a chlorine or bromine atom,
$R^1$ is a phenylcarbonylmethyl, benzyl, naphthylmethyl, pyridinylmethyl, pyrimidinylmethyl, quinolinylmethyl, isoquinolinylmethyl, quinazolinylmethyl, quinoxalinyl-methyl or naphthyridinylmethyl group in which the aromatic or heteroaromatic moiety is in each case mono- or disubstituted by $R_a$, where the substituents may be identical or different and $R_a$ is a hydrogen, fluorine or chlorine atom or a cyano, methyl, ethyl, methoxy or ethoxy group, $R^2$ is a methyl, ethyl, propyl, isopropyl, cyclopropyl or phenyl group and
$R^3$ is a 2-buten-1-yl, 3-methyl-2-buten-1-yl, 2-butin-1-yl, 2-fluorobenzyl, 2-chlorobenzyl, 2-bromobenzyl, 2-iodobenzyl, 2-methylbenzyl, 2-(trifluoromethyl)benzyl or 2-cyanobenzyl group.

The process is more preferable for those compounds in which
X is a chlorine or bromine atom,
$R^1$ is a cyanobenzyl, (cyanopyridinyl)methyl, quinolinylmethyl, (methylquinolinyl)methyl, isoquinolinylmethyl, (methylisoquinolinyl)methyl, quinazolinylmethyl, (methylquinazolinyl)methyl, quinoxazinylmethyl, (methylquinoxalinyl)methyl, (dimethylquinoxalinyl)methyl or naphthyridinylmethyl group,
$R^2$ is a methyl, cyclopropyl or phenyl group and
$R^3$ is a 2-buten-1-yl, 3-methyl-2-buten-1-yl, 2-butin-1-yl, 2-chlorobenzyl, 2-bromobenzyl or 2-cyanobenzyl group,
but in particular for the compounds 1-[(4-methylquinazolin-2-yl)methyl]-3-methyl-7-(2-butyn-1-yl)-8-(3-(R)-aminopiperidin-1-yl)-xanthine, 1-[(3-methylisoquinolin-1-yl)methyl]-3-methyl-7-(2-butyn-1-yl)-8-((R)-3-aminopiperidin-1-yl)-xanthine and 1-[(3-cyanopiperidin-2-yl)methyl]-3-methyl-7-(2-butyn-1-yl)-8-(3-(R)-aminopiperidin-1-yl)-xanthine, where X is bromine.

Preference is given in each case to using (R)-3-(phthalimido)piperidine as a reagent. The preparation of the compounds of the formula (III) has been described in the literature which has already been cited above and is effected by processes known per se.

The invention further provides a process for preparing optically active 3-(phthalimido)piperidine. In this process, 3-aminopyridine is initially hydrogenated by means of processes known per se. The thus obtained racemic 3-aminopiperidine is then converted to the corresponding phthalimide by means of phthalic anhydride. The (R) enantiomer can be precipitated selectively out of the solution of the racemic, crude phthalimide (IV) by means of D-tartaric acid. It is also possible to obtain the (S) enantiomer of (IV) in a simple manner from the mother liquor of this salt precipitation by adding L-tartaric acid, without preceding removal of the excess of D-tartaric acid still present in the mother liquor.

This extremely simple enantiomeric separation of the compound of the formula (IV) is surprising to those skilled in the art. The racemic base from the hydrogenation reaction does not have to be purified beforehand for this purpose. The process works without any problem even on the industrial scale.

In addition, the unexpectedly clean reaction of 3-aminopiperidine with phthalic anhydride is surprising per se, since, according to the literature (for example U.S. Pat. No. 4,005,208, especially Example 27), mixtures would be expected which, in addition to the desired product, comprise derivatives in which the ring nitrogen atom is acylated.

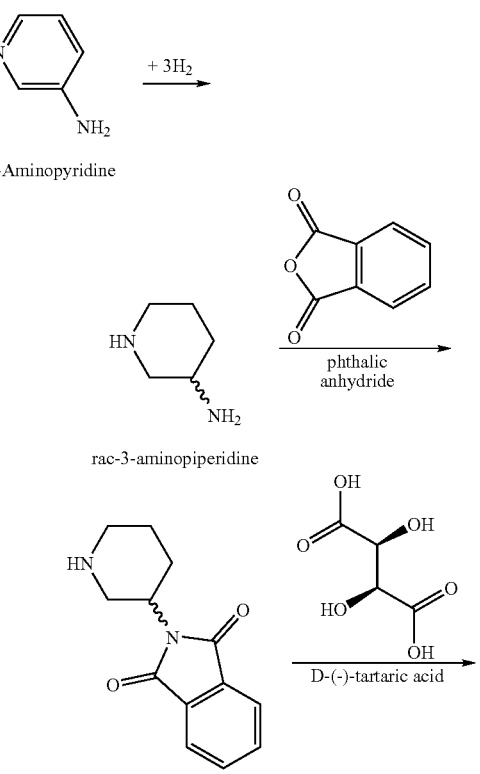

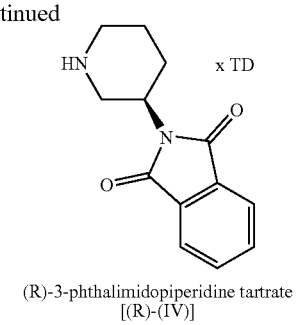

(R)-3-phthalimidopiperidine tartrate
[(R)-(IV)]

The examples which follow will illustrate the invention in greater detail:

EXAMPLE 1

D-Tartaric Acid Salt of the R Enantiomer of 3-(Phthalimido)Piperidine a. Hydrogenation:

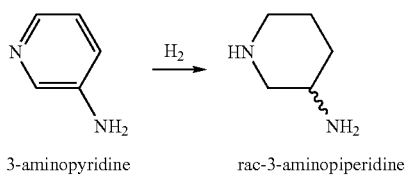 [SMILES: Nc1cccnc1 ; "H2" ; NC1CCCNC1]

3-aminopyridine → rac-3-aminopiperidine 10.00 kg (106.25 mol) of 3-aminopyridine, 500 g of technical-grade activated carbon and 65 liters of acetic acid are initially charged in a hydrogenation reactor. 50 g of Nishimura catalyst (a commercially available rhodium/platinum mixed catalyst) are added slurried in 2.5 liters of acetic acid and flushed in with 2.5 liters of acetic acid. Hydrogenation is effected at 50° C. and 100 bar of hydrogen pressure until hydrogen uptake stops and post-hydrogenation is subsequently effected at 50° C. for 30 minutes. The catalyst and the activated carbon are filtered off and washed with 10 liters of acetic acid. The product solution is reacted further without purification.

The reaction also proceeds under less severe pressures.

b. Acylation

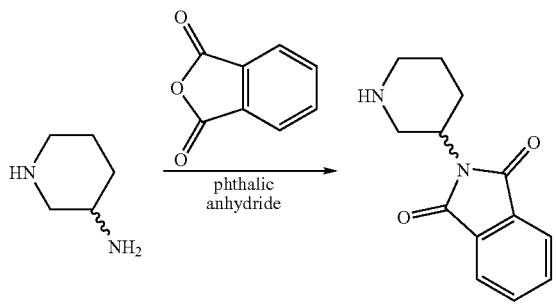 [SMILES: NC1CCCNC1 ; O=C1OC(=O)c2ccccc21 ; O=C1c2ccccc2C(=O)N1C1CCCNC1]

15.74 kg (106.25 mol) of phthalic anhydride are initially charged in the reactor and admixed with the filtrate from the hydrogenation. It is flushed in with 7.5 liters of acetic acid and the reaction mixture is subsequently heated to reflux, in the course of which approx. 30% of the acetic acid used is distilled off within one hour. The reaction solution is cooled to 90° C. The product solution is reacted further without purification.

c. Optical Resolution

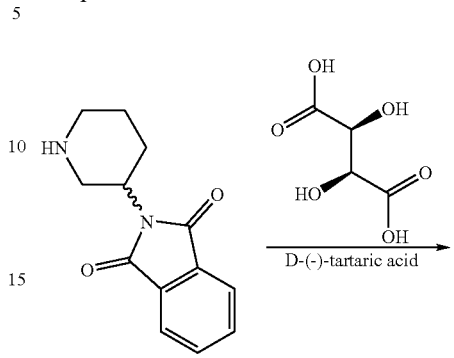

(R)-3-phthalimidopiperidine tartrate
[(R)-(IV)]

A solution, heated to 50° C., of 11.16 kg of D(−)-tartaric acid (74.38 mol) in 50 liters of absolute ethanol is metered into the acylation reaction solution at 90° C. It is flushed in with 10 liters of absolute ethanol and stirred at 90° C. for 30 minutes, in the course of which the product crystallizes. After cooling to 5° C., the product was centrifuged off and washed with absolute ethanol. The product solution is reacted further without purification.

d. Recrystallization

The moist crude product is heated to reflux in a mixture of 50 liters of acetone and 90 liters of water until a solution has formed. Subsequently, the solution is cooled to 5° C., in the course of which the product crystallizes out. The suspension is stirred at 5° C. for 30 minutes, and the product is centrifuged off and finally washed with a mixture of 20 liters of acetone and 10 liters of water. The mixture is dried at 45° C. in a drying cabinet under inertization.

Yields: 11.7-12.5 kg (29-31% of theory)

EXAMPLE 2

Synthesis of 1-[(4-methylquinazolin-2-yl)methyl]-3-methyl-7-(2-butin-1-yl)-8-(3-(R)-aminopiperidin-1-yl)-xanthine a. 2-Chloromethyl-4-methylquinazoline

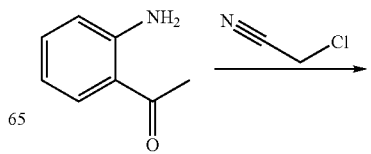

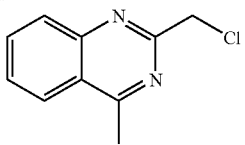

10.00 kg (73.98 mol) of 2-aminoacetophenone are initially charged and 24.5 liters of 1,4-dioxane are added. The solution, cooled to 10° C., is admixed with 16.72 kg (458.68 mol) of hydrogen chloride by blanketing. The reaction mixture warms up to 22-25° C. At this temperature, further hydrogen chloride is blanketed in. From about half of the total blanketing amount, the mixture is cooled to −10° C. and blanketing is continued. Subsequently, the suspension formed is left to stand at −10° C. overnight.

A solution of 6.70 kg (88.78 mol) of chloroacetonitrile in 2.5 liters of 1,4-dioxane is added at −10° C. within one hour. The feed vessel is flushed with 2 liters of 1,4-dioxane. Afterwards, the reactor contents are warmed to 6° C. and stirred for a further approx. 2 hours.

A further reactor is initially charged with a mixture of 122 liters of water and 62.04 kg (775.31 mol) of sodium hydroxide solution (50%) and cooled to 6° C. The reaction mixture from the first reactor is added in portions. The internal temperature is not more than 11° C. Subsequently, the first reactor is flushed first with 6 liters of 1,4-dioxane and then with 6 liters of water. The resulting suspension is stirred at 5° C. for a further 30 minutes. The product is centrifuged off, washed with 41 liters of water and dried at 35° C. in a drying cabinet under inertization.

Yield: 10.5-12.1 kg (74-85% of theory)

b. 1-[(4-Methylquinazolin-2-yl)methyl]-3-methyl-7-(2-butin-1-yl)-8-bromoxanthine

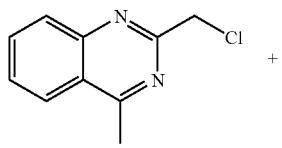

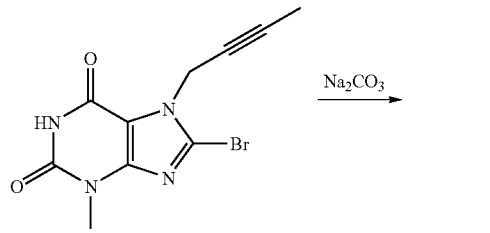

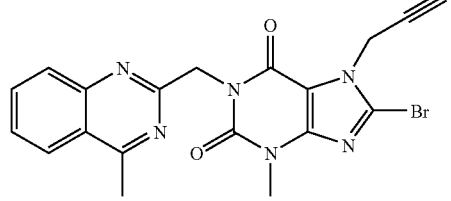

10.00 kg (33.66 mol) of 3-methyl-7-(2-butin-1-yl)-8-bromoxanthine, 7.13 kg (37.02 mol) of 2-chloromethyl-4-methylquinazoline, 3.92 kg (37.02 mol) of anhydrous sodium carbonate and 30 liters of N-methyl-2-pyrrolidone are initially charged in the reactor. The reactor contents are heated to 140° C. and stirred at 140° C. for 2 hours. After the reaction has ended, the reaction mixture is cooled to 80° C. and diluted with 60 liters of 96% ethanol and subsequently at 70° C. with 55 liters of water. At 60° C., 4.04 kg (67.32 mol) of acetic acid are metered in and flushed in with 5 liters of water. The resulting suspension is stirred at 60° C. for 30 minutes, then cooled to 23° C. and stirred for a further 30 minutes. Subsequently, the product is centrifuged off and washed first with a mixture of 20 liters of 96% ethanol and 20 liters of water, then with 40 liters of 96% ethanol and 40 liters of water. Drying is effected at 45° C. in a drying cabinet under inertization.

Yield: 11.6-12.6 kg (76-83% of theory)

c. 1-[(4-Methylquinazolin-2-yl)methyl]-3-methyl-7-(2-butin-1-yl)-8-(3-(R)-phthalimidopiperidin-1-yl)-xanthine

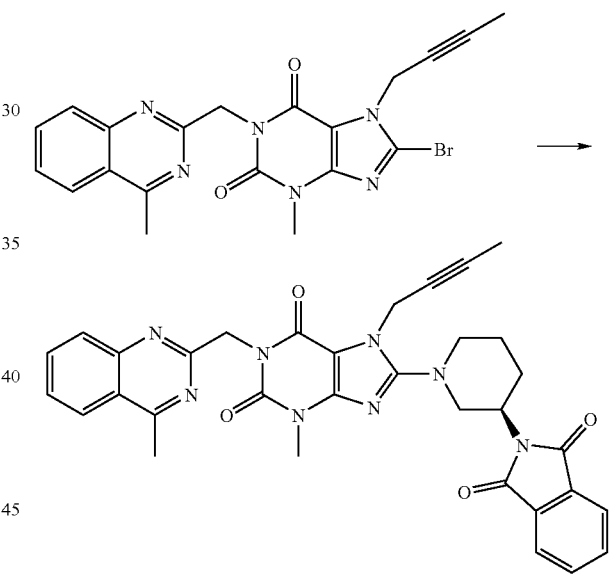

10.00 kg (22.06 mol) of 1-[(4-methylquinazolin-2-yl)methyl]-3-methyl-7-(2-butin-1-yl)-8-bromoxanthine, 12.59 kg (33.09 mol) of 3-(phthalimido)piperidine D-tartrate and 17.5 liters of N-methyl-2-pyrrolidone are initially charged in the reactor. The reactor contents are heated to 140° C. After the temperature has been attained, 11.41 kg (88.24 mol) of diisopropylethylamine are metered in within 20 minutes. The feed vessel is flushed with 2.5 liters of N-methyl-2-pyrrolidone and the reaction mixture is subsequently stirred at 140° C. for 2 hours. After the reaction has ended, the reaction mixture is cooled to 60° C. and diluted with 80 liters of methanol. The resulting suspension is stirred at 50° C. for 30 minutes, then cooled to 23° C. and stirred for a further 30 minutes. Subsequently, the product is centrifuged off and washed 3 times with 20 liters each time of methanol. Drying is effected at 45° C. in a drying cabinet under inertization.

Yield: 12.0-12.5 kg (90-94% of theory)

d. 1-[(4-Methylquinazolin-2-yl)methyl]-3-methyl-7-(2-butin-1-yl)-8-(3-(R)-aminopiperidin-1-yl)-xanthine

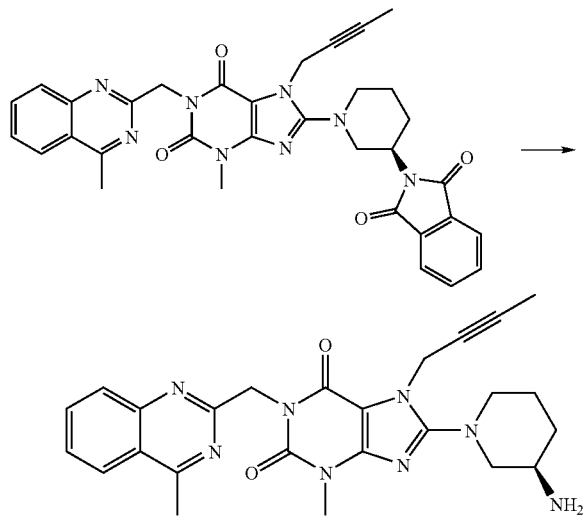

1800 kg (3 mol) of 1-[(4-methylquinazolin-2-yl)methyl]-3-methyl-7-(2-butin-1-yl)-8-(3-(R)-phthalimidopiperidin-1-yl)-xanthine are heated to 80-85° C. in 18 liters of toluene. Subsequently, 1.815 liters (30 mol) of ethanolamine are added to the suspension at 75-80° C. To complete the reaction, the mixture is stirred at 80-85° C. for 2 hours, in the course of which the solids go into solution. Subsequently, the phases are separated. The ethanolamine phase is washed twice with warm toluene (4 liters each time). The combined toluene phases are washed twice with 8 liters each time of water at 75-80° C. From the toluene phase, 22 liters of toluene are distilled off under reduced pressure. 4 liters of tert.-butyl methyl ether are metered at 40-50° C. to the resulting suspension and subsequently cooled to 0-5° C. The product is isolated by filtration, washed with tert.-butyl methyl ether and suction-dried. The moist crude substance is subsequently heated to reflux with 5 times the amount of absolute ethanol and the hot solution is clarified by filtration through activated carbon. After the filtrate has been cooled to 20° C. and crystallization has set in, it is diluted to double the volume with tert.-butyl methyl ether. The suspension is cooled to 2° C., stirred for a further 2 hours, filtered with suction and dried at 45° C. in a vacuum drying cabinet.

Yield: 1174 g (83.2% of theory)

e. Alternative Process for Step d 1400 g (2.32 mol) of 1-[(4-methylquinazolin-2-yl)methyl]-3-methyl-7-(2-butin-1-yl)-8-(3-(R)-phthalimidopiperidin-1-yl)-xanthine are initially charged in 4.9 l of tetrahydrofuran and subsequently heated to 55-65° C. Subsequently, 350 ml of water and 1433 g (2.32 mol) of ethanolamine are added to the suspension. To complete the reaction, the mixture is stirred at 60-63° C. for a further 3 hours.

Subsequently, 619 ml of 45% sodium hydroxide solution and 3.85 l of water are added and the mixture is stirred at 55-65° C. for 30 min.

5.6 l of toluene are then added to the reaction mixture, the mixture is stirred for 15 min and the phases are subsequently separated.

The organic phase is washed with 2.8 l of water at 55-65° C. and subsequently removed. From the organic phase, 4.2 l are distilled off under reduced pressure. Subsequently, 1.4 l of methylcyclohexane are added at 65-75° C., in the course of which the product crystallizes. The suspension is stirred at 15-25° C. for 8-16 h and subsequently cooled to 0-5° C. The product is isolated by filtration, washed with 4.2 l of methylcyclohexane, suction-dried and dried at 35° C. under reduced pressure.

The dried crude substance (991 g) is subsequently heated to reflux with 5 times the amount of methanol, activated carbon is added and the mixture is filtered. The filtrate is reduced to a volume of 1.5 l by distilling off methanol. After the filtrate has been cooled to 45-55° C., it is diluted to four times the volume with tert.-butyl methyl ether. The suspension is cooled to 0-5° C., stirred for 2 hours, filtered with suction, washed with tert.-butyl methyl ether and dried at 35° C. in a vacuum drying cabinet.

Yield: 899 g (81.9% of theory)

EXAMPLE 3

1-[(3-Cyanopyridin-2-yl)methyl]-3-methyl-7-(2-butin-1-yl)-8-(3-(R)-aminopiperidin-1-yl)-xanthine a. 3-Cyano-2-(chloromethyl)-pyridine 165.5 g (0.98 mol) of 2-hydroxymethyl-3-pyridinecarboxamide are heated together with 270 ml of phosphorus oxychloride to 90-100° C. for 1 hour. The reaction mixture is cooled to room temperature and subsequently added dropwise to approx. 800 ml of water at 50-60° C. After the phosphorus oxychloride has been hydrolyzed, the mixture is neutralized with sodium hydroxide solution with cooling, in the course of which the product precipitates out. It is filtered off, washed with 300 ml of water and subsequently dried at 35-40° C.

Yield: 122.6 g (82% of theory)

Variant to Process Step a:
3-cyano-2-(chloromethyl)pyridine 20.0 g (131.45 mmol) of 2-hydroxymethyl-3-pyridinecarboxamide are suspended in 110 ml of acetonitrile and heated to 78° C. Within 15 minutes, 60.65 g (395.52 mmol) of phosphorus oxychloride are metered in and the mixture is heated to 81° C. for 2 hours. After cooling at 22° C., the reaction mixture is stirred into 200 ml of water at 40° C. After 100 ml of toluene have been added, the mixture is neutralized with sodium hydroxide solution with cooling. After phase separation, the organic phase is washed with 100 ml of water. Removal of the organic phase and evaporation of the solvent under reduced pressure gives rise initially to an oily residue which crystallizes on standing.

Yield: 16.66 g (83% of theory)

b. 1-[(3-Cyanopyridin-2-yl)methyl]-3-methyl-7-(2-butin-1-yl)-8-bromoxanthine

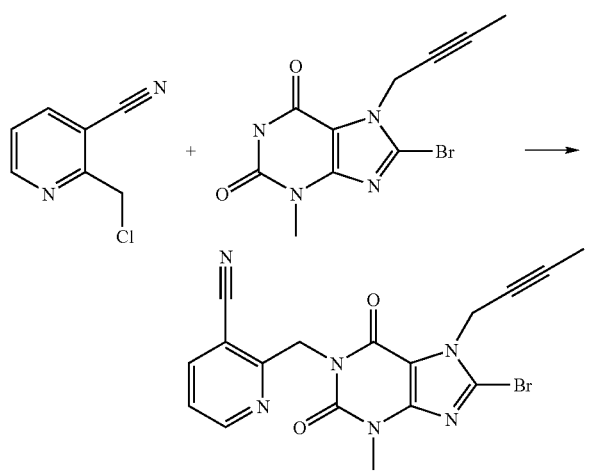

202 g (0.68 mol) of 3-methyl-7-(2-butin-1-yl)-8-bromoxanthine, 188.5 g (1.36 mol) of anhydrous potassium carbonate and 1.68 liters of N-methyl-2-pyrrolidone are initially charged in the reactor and heated to 70° C. Subsequently, 119 g (0.75 mol) of 2-chloromethyl-3-cyanopyridine in 240 ml of N-methyl-2-pyrrolidine (NMP) are added dropwise. The reactor contents are stirred at 70° C. for 19 hours. After the reaction has ended, 2.8 liters of water are added to the reaction mixture and it is cooled to 25° C. The product is filtered off, washed with 2 liters of water and dried at 70° C. in a drying cabinet under inertization.

Yield: 257.5 g (91% of theory)

c. 1-[(3-Cyanopyridin-2-yl)methyl]-3-methyl-7-(2-butin-1-yl)-8-(3-(R)-phthalimidopiperidin-1-yl)-xanthine

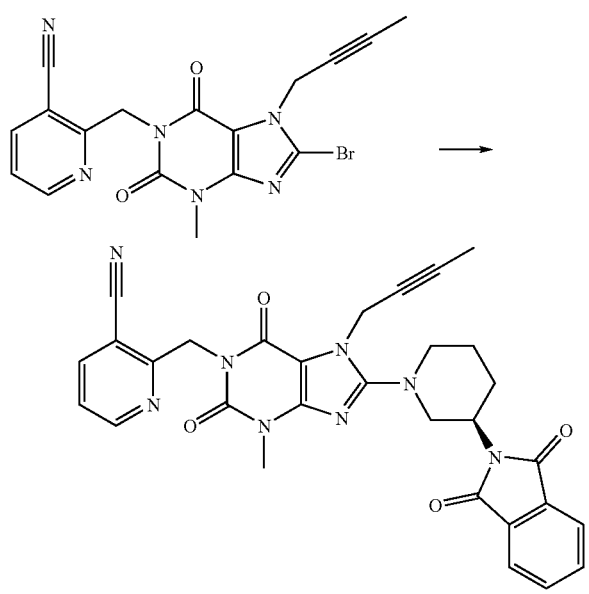

230 g (0.557 mol) of 1-[(3-cyanopyridin-2-yl)methyl]-3-methyl-7-(2-butin-1-yl)-8-bromoxanthine, 318 g (0.835 mol) of 3-(phthalimido)piperidine D-tartrate and 1.15 liters of N-methyl-2-pyrrolidone are initially charged in the reactor. The reactor contents are heated to 140° C. After the temperature has been attained, 478 ml (2.78 mol) of diisopropylethylamine are metered in within 20 minutes and the reaction mixture is subsequently stirred at 140° C. for 2 hours. Subsequently, the reaction mixture is cooled to 75° C. and diluted with 720 ml of methanol. Afterwards, 2.7 liters of water are added at 68-60° C. and the mixture is cooled to 25° C. The product is filtered off and washed with 2 liters of water. Drying is effected at 70° C. in a drying cabinet under inertization.

The crude product thus obtained is subsequently stirred at boiling in 1 liter of methanol, hot-filtered, washed with 200 ml of methanol and subsequently dried at 70° C. under inertization.

Yield: 275 g (88% of theory)

d. 1-[(3-cyanopyridin-2-yl)methyl]-3-methyl-7-(2-butin-1-yl)-8-(3-(R)-aminopiperidin-1-yl)-xanthine

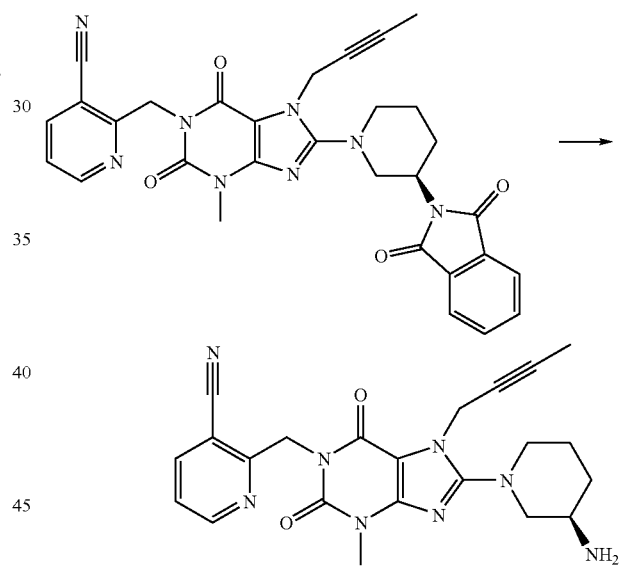

412.5 g (0.733 mol) of 1-[(3-cyanopyridin-2-yl)methyl]-3-methyl-7-(2-butin-1-yl)-8-(3-(R)-phthalimidopiperidin-1-yl)-xanthine are heated to 80° C. in 4125 ml of toluene. Subsequently, 445 ml of ethanolamine (7.33 mol) are added to the suspension at 75-80° C. To complete the reaction, the mixture is stirred at 80-85° C. for a further 2 hours, in the course of which the solids go into solution. Subsequently, the phases are separated. The ethanolamine phase is extracted twice with warm toluene (1 liter each time). The combined toluene phases are washed twice with 2 liters each time of water at 75-80° C. The toluene phases are dried with sodium sulphate, filtered and subsequently reduced to a volume of approx. 430 ml by distillation under reduced pressure. Subsequently, 1 liter of tert.-butyl methyl ether is metered in at 50-55° C. and the mixture is then cooled to 0-5° C. The product is isolated by filtration, washed with tert.-butyl methyl ether and dried at 60° C. in a drying cabinet.

Yield: 273 g (86% of theory); Melting point: 188±3° C.

Analogously to Examples 2 and 3, 1-[(3-methylisoquinolin-1-yl)methyl]-3-methyl-7-(2-butin-1-yl)-8-((R)-3-aminopiperidin-1-yl)-xanthine is also prepared.

What is claimed is:
1. (R)-3-(Phthalimido)piperidine D-tartrate.
2. (S)-3-(Phthalimido)piperidine L-tartrate.

\* \* \* \* \*